United States Patent [19]

Cosyns et al.

[11] 4,347,392

[45] * Aug. 31, 1982

[54] PROCESS FOR THE SELECTIVE HYDROGENATION OF A HYDROCARBON FRACTION WITH 2 OR 3 CARBON ATOMS PER MOLECULE

[75] Inventors: Jean Cosyns, Maule; Daniel Durand, Rueil-Malmaison; Gérard Léger, St. Genis les Ollieres, all of France

[73] Assignee: Institut Francais du Petrole, Rueil-Malmaison, France

[*] Notice: The portion of the term of this patent subsequent to Oct. 28, 1997, has been disclaimed.

[21] Appl. No.: 157,764

[22] Filed: Jun. 9, 1980

[30] Foreign Application Priority Data

Jun. 8, 1979 [FR] France .................................. 79 14925

[51] Int. Cl.³ ............................ C07C 5/08; C07C 7/00
[52] U.S. Cl. ...................................... 585/259; 585/260
[58] Field of Search ................................ 585/259, 260

[56] References Cited

U.S. PATENT DOCUMENTS 3,116,342  12/1963  Robinson et al. ................... 585/260
3,898,298  8/1975   Desiderio et al. ................... 585/265
4,230,897  10/1980  Cosyns et al. ....................... 585/260

Primary Examiner—Earl C. Thomas
Assistant Examiner—Wayne A. Langel
Attorney, Agent, or Firm—Millen & White

[57] ABSTRACT

A $C_2$ or $C_3$ hydrocarbon fraction comprising at least one mono-olefinic hydrocarbon and at least one acetylenic hydrocarbon, and optionally at least one diolefinic hydrocarbon, is hydrogenated selectively in contact with a palladium-on-alumina catalyst subjected to calcining at a relatively high temperature and whose palladium crystallites have an average size of at least 50 Angströms.

9 Claims, No Drawings

PROCESS FOR THE SELECTIVE HYDROGENATION OF A HYDROCARBON FRACTION WITH 2 OR 3 CARBON ATOMS PER MOLECULE

This invention relates to a process for selectively hydrogenating impurities of an ethylene and/or propylene cut.

A process has been described, in a prior patent application (Ser. No. 026,984 filed Apr. 4, 1979, now U.S. Pat. No. 4,230,897 issued Oct. 28, 1980), for hydrogenating a hydrocarbon fraction comprising at least one diolefinic hydrocarbon and at least one acetylenic hydrocarbon, wherein the acetylenic hydrocarbon hydrogenates, and not the diolefinic hydrocarbon. A catalyst of palladium on alumina was used, whose average crystallite size was at least 50 Angströms.

The processes for converting hydrocarbons at a high temperature, such as, for example, steam-cracking, provide unsaturated hydrocarbons such as, for example, ethylene, propylene, butadiene, butenes and hydrocarbons boiling in the gasoline range; the gaseous monoolefinic hydrocarbons with two or three carbon atoms, obtained by this process, also contain an amount of hydrocarbons of greater unsaturation degree. The content of these hydrocarbons depends on the severity of the conversion treatment but is always too low to permit their separation and their use as such in the petrochemical field. This is the case of the ethylene or propylene cuts from which acetylene or propyne and propadiene must be removed as completely as possible.

For manufacturing pure propylene, the known processes tend to hydrogenate propyne and propadiene of the $C_3$ cut as selectively as possible. A typical steam-cracking charge contains, by weight, 2 to 5% of propane, 90 to 95% of propylene, 2 to 3% of propyne and 1 to 2% of propadiene.

The required purity of propylene for petrochemical uses usually corresponds to less than 10 ppm of the propyne + propadiene amount. It is also desired that the propylene yield be at least 100% and more generally higher than 100% since propyne and propadiene can hydrogenate selectively to propylene.

A selective hydrogenation catalyst must have two essential qualities: high selectivity, so as to hydrogenate selectively the acetylenic, allenic and diolefinic impurities while avoiding parasitic reactions of monoolefin hydrogenation and polymerization which, not only decrease the yield, but deactivate the catalyst.

The most common catalysts up to now consist of palladium deposited on a silica or alumina carrier.

With these conventional catalysts, 0.3 to 1% by weight of oligomers are present in the hydrogenation product. The present invention proposes the use of catalysts which have not these disadvantages, the oligomer content of the product being in most cases lower than 0.2% by weight.

A first particular case for using the process is the hydrogenation of a $C_2$ cut comprising, for example, 60 to 98% of ethylene, 0.2 to 5% of acetylene and 0 to 35% of ethane by volume.

Another particular case for using the process is the hydrogenation of $C_3$ cuts comprising at least 80% b.w. of propylene, 1 to 5% b.w. of propyne, 0.5 to 5% b.w. of propadiene and 0 to 15% b.w. of propane.

The process of the invention comprises hydrogenating the cut in contact with a catalyst of palladium on alumina, the average size of the palladium crystallites being at least 50 Angströms. This size may be determined, for example, by electronic microscopy. A catalyst complying with this definition may be prepared by incorporating a palladium compound to alumina, in a proportion of 0.1 to 5% by weight of palladium with respect to alumina, followed with heat-activation at a temperature of 600° to 1100° C., preferably 700° to 950° C., said heating being conducted in a neutral atmosphere, for example in nitrogen, in a reducing atmosphere, for example in hydrogen, or in an oxidizing atmosphere, for example in a gas containing free oxygen. An oxidizing atmosphere is however preferred since the palladium crystallites form very quickly in that case. The operation may be conducted under any pressure, for example under normal pressure. The treatment may be followed, if necessary, with a reduction treatment, for example with hydrogen, according to a known technique; the reduction temperature is preferably in the range from 0° to 200° C.

The method for incorporating the palladium compound may be of any type, for example, admixing in the dry state or in the presence of water, or impregnation with a solution of a palladium compound. The palladium compound may be any one of the palladium compounds known and/or proposed for an equivalent use, for example, palladium nitrate, palladium chloride or palladium acetylacetone. In certain cases, other metals having a co-catalytic effect may be added.

Alumina carriers of low acidity, of a specific surface lower than 100 $m^2/g$, are preferred in the invention.

The use of activation temperatures lower than those selected for the invention results to catalysts whose average crystallite size is lower than 45 Å; these catalysts are responsible of an excessive formation of oligomers.

The selective hydrogenation may be conducted at a temperature of about 0° to 160° C. The operation may be of the gas phase or liquid phase type. In the latter case, which is particularly advantageous for a $C_3$ cut, the pressure must be sufficient to maintain a liquid phase and it is preferably operated at 0°–80° C., under 10 to 40 bars, at a liquid feed rate of 2 to 50, preferably 10 to 30 volumes per volume of catalyst per hour. In gas phase, the flow rate of the $C_2$ and/or $C_3$ cut (VVH gas) is, for example 500 to 20,000 volumes per volume of catalyst per hour, and the pressure, for example, 5 to 30 bars.

The molar ratio of hydrogen to the unsaturated hydrocarbons to be hydrogenated (acetylenics + optionally diolefinics) is usually from 1:1 to 5:1, preferably 1:1 to 2:1.

According to an alternative embodiment, it can be operated in at least two successive catalytic zones. The catalyst of the first zone is the above catalyst having palladium crystallites of an average size of at least 50 Å; the catalyst of at least the last zone is a conventional catalyst of palladium on alumina whose average crystallite size is not larger than 45 Å.

It is advantageous, in that case, to use 5 to 70%, and preferably 20 to 60% by volume of the large crystallite catalyst (50 Å or more), the remainder being the conventional catalyst. It is advantageous to convert 50–90% of the acetylenic and diolefinic hydrocarbons in contact with the first catalyst, and to terminate in contact with the second catalyst, for example, up to a conversion degree of 92% or more.

The conventional small crystallite catalyst is obtained in the same manner as the large crystallite catalyst, except that the calcination is operated at a temperature below 600° C., for example, at 300°-550° C.

Hydrogen is used, according to the invention, in the pure state or diluted with inert gases, for example, with methane.

EXAMPLE 1 (COMPARISON)

A catalyst is prepared by impregnating an alumina carrier in the form of balls of a 2 mm diameter, having a specific surface of 57 m$^2$/g and a total pore volume of 0.6 cc/g, with a nitric acid, solution of palladium nitrate, so as to obtain 0.3% by weight of palladium in the resultant catalyst. After impregnation, the catalyst is dried at 120° C. in a drying oven and calcined at 450° C. for 2 hours in an air stream.

A sample of the catalyst is reduced by passing hydrogen at 100° C. for 2 hours; it is then examined by electronic microscopy. The palladium crystallites are found to have an average size of 35 Å. The catalyst is introduced into a tubular reactor and reduced in situ by passing hydrogen at 100° C. for 2 hours.

The operating conditions are the following:

| | |
|---|---|
| Space velocity (liquid VVH) | 20 |
| Pressure | 20 bars |
| Temperature | 20° C. |
| H$_2$/propyne + propadiene | 1.2 mole/mole. |

The analyses of the charge and the resultant product are tabulated below:

| COMPOUND | FEEDSTOCK % b.w. | PRODUCT % b.w. |
|---|---|---|
| Propane | 4.0 | 6.0 |
| Propylene | 91.5 | 93.4 |
| Propyne | 2.7 | not detectable |
| Propadiene | 1.8 | about 5 ppm |
| Oligomers | — | 0.6 |
| TOTAL | 100 | 100 |

It is found that the catalyst is active and selective since the specification for the residual content of propyne and propadiene is easily attained and the propylene yield is 93.4/91.5, thus 102%. However the oligomer content amounts to 0.6% b.w.

EXAMPLE 2 (according to the invention)

A catalyst containing, once prepared, 0.3% b.w. of palladium is manufactured as in example 1. The catalyst is dried as in example 1, but it is calcined under different temperature conditions, the latter being 900° C. for 2 hours.

A sample of the catalyst is examined by electronic microscopy; after reduction in a hydrogen stream at 100° C. for 2 hours, an average crystallite diameter of 80 Å is found. The catalyst is introduced into a reactor and reduced as stated in example 1.

The resultant product has the following composition:

| | % by weight |
|---|---|
| Propane | 6.2 |
| Propylene | 93.65 |
| Propyne | not detectable |
| Propadiene | 8 ppm |
| Oligomers | 0.15 |
| TOTAL | 100 |

It is found that, with the catalyst of the invention, the content of resultant oligomers has been strongly reduced, while the activity and the selectivity remain excellent. The propylene yield is 93.65/91.5, thus 102.3%, a value slightly higher than with the conventional catalyst. The propadiene content is slightly higher but remains largely below the conventional specifications.

EXAMPLE 3 (comparison)

In this example, a catalyst is prepared by impregnating the same alumina carrier as in example 1; however the palladium nitrate content of the impregnation solution is so decreased as to introduce 0.045% by weight of Pd, instead of 0.3%. After impregnation, the catalyst is dried and calcined at 400° C. as in example 1. A sample of the catalyst is reduced by passing H$_2$ at 100° C. for 2 hours; it is then examined by electronic microscopy and the average crystallite size is found to be 30 Å. The catalyst is then introduced as a fixed bed into a tubular reactor and reduced in situ by passing H$_2$ at 100° C. for 2 hours.

A C$_2$ steam-cracking gas cut, whose composition is as follows:

| | |
|---|---|
| acetylene | 1% by vol. |
| ethylene | 80% by vol. |
| ethane | 19% by vol. | is treated in the following operating conditions:

| | |
|---|---|
| total pressure | 25 bars |
| VVH gas | 2,500 h$^{-1}$ |
| initial temperature | 80° C. |
| H$_2$/acetylene molar ratio | 2.3 |

The added hydrogen contains carbon monoxide in such an amount that the total gas mixture (C$_2$ cut+H$_2$) contains 80 ppm by mole of CO, to further increase the selectivity. The gas product obtained after after 100 hours has the following composition:

| | |
|---|---|
| ethylene | 79.7% by vol. |
| acetylene | ≦2 ppm by vol. |
| ethane | 20.3% by vol. |

However, after cooling, a liquid phase condenses; it corresponds to oligomers consisting of hydrocarbons with 4 to 20 carbon atoms. The approximate composition of this cut is the following:

| | |
|---|---|
| C$_4$ | 70% |
| C$_6$ | 20% |
| C$_8$ | 5% |
| C$_{10}$+ | 5% |

The total amount of this liquid phase corresponds to 2000 ppm by weight of the total amount of treated gas. A portion of the C$_{10}$+ fraction fills up the pores of the catalyst and fouls it progressively, so that the performance (≦2 ppm of acetylene) is only maintained by increasing the temperature progressively up to about 150° C., which is attained after 2 months of run. At that moment, even if increasing the temperature above 150° C., the product specification is no longer attained and the catalyst must be regenerated.

EXAMPLE 4 (according to the invention)

A catalyst is prepared as in example 3, as concerns the carrier and the palladium content (0.045% by weight); however the calcination is operated at 900° C. as in example 2, according to the invention. A sample of this catalyst is reduced by passing hydrogen at 100° C. for 2 hours; it is then examined by electronic microscopy and the average crystallite size is found to be 85 Å.

The catalyst is then tested in the same conditions and with the same charge as in example 3. The resultant product, after about 100 hours, has the following composition:

| | |
|---|---|
| ethylene | 79.6% |
| acetylene | ≦2 ppm |
| ethane | 20.4% |

The amount of oligomers collected in liquid phase corresponds to 500 ppm by weight of the gas cut.

After 2 months, the product specification is yet attained easily. The final cycle temperature of 150° C. is attained after 6 months only. This shows the advantage of the catalyst prepared according to the invention.

What is claimed is:

1. A process for selectively hydrogenating a $C_2$ and/or $C_3$ hydrocarbon fraction comprising at least one mono-olefinic hydrocarbon, at least one acetylenic hydrocarbon, and at least one diolefinic hydrocarbon, to selectively hydrogenate the acetylenic hydrocarbon and the diolefinic hydrocarbon, without substantial hydrogenation of the mono-olefinic hydrocarbon, comprising contacting said hydrocarbon fraction and hydrogen with a catalyst of palladium-on-alumina, with the average size of the palladium crystallites in said catalyst being at least 50 Angströms.

2. A process according to claim 1, wherein the catalyst is obtained by admixing alumina with at least one palladium compound and subsequently heating the admixture to a temperature of 650° to 1100° C.

3. A process according to claim 2, wherein the heating is conducted at 750°–950° C.

4. A process according to claim 2, wherein the heating is conducted in a free oxygen containing atmosphere.

5. A process according to claim 2, wherein the heating is followed with a reduction treatment with hydrogen.

6. A process according to claim 1, wherein said contacting is first conducted in part by passing said fraction and hydrogen over said catalyst with palladium crystallites having an average size of at least 50 Angströms, and further comprising continuing the contacting by passing resultant contacted fraction and hydrogen over a subsequent catalyst having palladium crystallites on alumina, the average size of the crystallites of said subsequent catalyst being at most 45 Angströms.

7. A process according to claim 6, wherein 5 to 70% of the total volume of the two catalysts is formed of the catalyst having an average crystallite size of at least 50 Angströms, and the remainder consisting of said catalyst having an average crystallite size of at most 45 Angströms.

8. A process according to claim 1, wherein the hydrocarbon fraction contacted is a substantially $C_2$ fraction containing about 60 to 98% by weight of ethylene, 0.2 to 5% by weight of acetylene and 0 to 35% by weight of ethane.

9. A process for selectively hydrogenating a $C_3$ hydrocarbon fraction containing simultaneously at least 80% by weight of propylene, 1 to 5% by weight of propyne, and 0.5 to 5% by weight of propadiene, to selectively hydrogenate the propyne and propadiene without substantial hydrogenation of the propylene, the process comprising contacting said hydrocarbon fraction and hydrogen with a catalyst of palladium on alumina, with the average size of the palladium crystallites in said catalyst being at least 50 Angströms.

* * * * *